(12) United States Patent
Constantz

(10) Patent No.: US 6,394,096 B1
(45) Date of Patent: May 28, 2002

(54) METHOD AND APPARATUS FOR TREATMENT OF CARDIOVASCULAR TISSUE MINERALIZATION

(75) Inventor: Brent R. Constantz, Portola Valley, CA (US)

(73) Assignee: Corazon Technologies, Inc., Menlo Park, CA (US)

( * ) Notice: Subject to any disclaimer, the term of this patent is extended or adjusted under 35 U.S.C. 154(b) by 0 days.

(21) Appl. No.: 09/118,193

(22) Filed: Jul. 15, 1998

(51) Int. Cl.[7] .................................................. A61B 19/00
(52) U.S. Cl. ....................................... 128/898; 604/507
(58) Field of Search ............................ 128/898; 604/27, 604/28, 96.01, 101.01, 101.05, 103.07, 916, 507

(56) References Cited

U.S. PATENT DOCUMENTS

| | | |
|---|---|---|
| 4,445,892 A | 5/1984 | Hussein et al. |
| 4,573,966 A | 3/1986 | Weikl et al. |
| 4,610,662 A | 9/1986 | Weikl et al. |
| 4,636,195 A | 1/1987 | Wolinsky |
| 4,655,746 A | 4/1987 | Daniels et al. |
| 4,824,436 A | 4/1989 | Wolinsky |
| 4,911,163 A | 3/1990 | Fina |
| 4,976,733 A | 12/1990 | Giradot |
| 5,059,178 A | 10/1991 | Ya |
| 5,069,664 A | 12/1991 | Guess et al. |
| 5,090,960 A | 2/1992 | Michael |
| 5,135,484 A * | 8/1992 | Wright ........................ 604/28 |
| 5,167,628 A | 12/1992 | Boyles |
| 5,195,955 A | 3/1993 | Michael |
| 5,222,941 A | 6/1993 | Michael |
| 5,380,284 A | 1/1995 | Michael |
| 5,443,446 A | 8/1995 | Shturman |
| 5,735,811 A * | 4/1998 | Brisken ....................... 604/22 |

* cited by examiner

*Primary Examiner*—Corrine McDermott
*Assistant Examiner*—Thomas Barrett
(74) *Attorney, Agent, or Firm*—Bret E. Field; Bozicevic, Field & Francis

(57) ABSTRACT

A method and several assemblies for the reducing of mineralization of cardiovascular tissue in vivo is provided. The method involves contacting cardiovascular tissue, such as a valve or a vessel, with an acidic treatment solution. One apparatus is a balloon catheter assembly for the infusion of an acidic treatment solution into a define area of a cardiovascular tissue. A second apparatus is a flexible cup which forms a defined area with the wall of a vessel for the introduction of an acidic treatment solution for the reduction of mineralization of a vessel. A third apparatus is an assembly for the introduction of an acidic treatment solution on one side of a valve, and the removal of the acidic treatment solution from the opposite side of the valve. Each apparatus can take the form of an elongated catheter for use in minimally invasive procedures or as hand held devices for use in an open surgical field.

22 Claims, 4 Drawing Sheets

METHOD AND APPARATUS FOR TREATMENT OF CARDIOVASCULAR TISSUE MINERALIZATION

FIELD OF THE INVENTION

This invention relates to a method and apparatus for reducing mineralization of a cardiovascular tissue in a subject, particularly to the use of an acid treatment solution for reducing mineralization of cardiovascular tissue such as a vessel or a valve.

BACKGROUND OF THE INVENTION

Atherosclerosis is commonly understood to be a deposition of cholesterol in the vessels of the cardiovascular system. An additional significant complication is pathologic calcification, which takes place both in blood vessels and in heart tissue. Cardiovascular bioprostheses also host calcific deposits that may severely limit longevity and performance of the device. Calcium deposits have been shown to be calcium phosphates that contain several inorganic components such as carbonate, acidic phosphate, sodium, magnesium, and fluoride (Tomazic, B. B., et al., *Ann. Thorac. Surg.* 60(2 Suppl.):S322–S327, 1995). All deposits, regardless of the site of formation, are carbonated apatites that contain an appreciable fraction of carbonate (Tomazic, B. B., et al., *Atherosclerosis* 69:5–19, 1988). It has been suggested that octacalcium phosphate ($Ca_4H(PO_4)_3 \cdot 2.5 H_2O$), could be a precursor mineral in the formation of cardiovascular calcium deposits, however the mechanism is in fact poorly understood (see Tomazic, B. B., In: *Hydroxyapatite and Related Materials*, pp. 93–115, P. W. Brown and B. Constantz, eds., CRC Press, Brown, Boca Ratan, Fla., 1994, herein incorporated by reference).

Surgical implantation of prosthetic devices (prosthesis) into humans and other mammals has been carried out with increasing frequency in the United States. Such protheses include heart valves, vascular grafts, urinary bladders, heart bladders, left ventricular-assist devices, hip prosthesis, breast implants, and tendon prosthesis, amongst others. At least forty models of substitute heart valves, including mechanical and bioprosthetic valves, have been used in the United States. Mechanical heart valve prostheses typically are composed of rigid materials such as polymers and metals, and use a poppet occluder which responds to changes in intracardiac pressure or flow. Bioprostheses have also been utilized for the replacement of heart valves. These are usually fabricated from porcine aortic valves or bovine epicardium, although only the porcine aortic valve or, occasionally, valves fashioned from human tissue, are used in the United States (see Hancock, E. W., in: *Scientific American Medicine*, Vol. 1, Section 1, Ch. IX, pp. 1–16, D. C. Dale and D. D. Friedman (eds)., Scientific American, N.Y., 1997).

Bioprostheses are typically pretreated with glutaraldehyde and then sewn onto a flexible metallic alloy or a flexible polymeric (plastic) stent which is then coved with a poly(ethylene terephthalate) cloth ring covering. Tissue valves are less likely than mechanical valves to produce thrombosis and systemic embolism. In addition, bioprostheses generally do not require routine anticoagulation. However, bioprostheses structurally deteriorate over time. This deterioration is usually related to mineralization (especially calcification) of the valve leaflets. Calcification is an important limitation on the useful life expectancy of bioprosthetic valves, and accounts for over sixty percent of the cardiac bioprostheses failures. Calcification of bioprosthetic valves develops more rapidly in children, which have an incidence of calcification of about 40% to 50% at four years. Adults have an incidence of calcification of between 5% to 20% at ten years (Carpentier, A., et al., *Circulation* 70 (suppl. I):I165–I168, 1984). Calcification causes thickening, retraction and reduced mobility of the leaflets and can lead to stenosis, insufficiency, or both. Currently, treatment of a functionally compromised bioprosthetic valve requires replacement with a new valve.

Several strategies to decrease or prevent mineralization of bioprosthetic heart valves have been described. Generally the methods involve treating the tissue with substances prior to implantation. Examples of pretreatment solutions to prevent calcification are a water-soluble phosphate ester (e.g., sodium dodecyl hydrogen phosphate, see U.S. Pat. No. 4,402,697), a water soluble quaternary ammonium salt (e.g., dodecyltrimethyammonium chloride, see U.S. Pat. No. 4,405,327), a sulfated higher aliphatic alcohol, (e.g., sodium dodecyl sulfate, see U.S. Pat. No. 4,323,358), or covalent coupling of an aliphatic carboxylic acid (see U.S. Pat. No. 4,976,733). Treatment of a bioprosthesis with a buffered solution having a pH in the range of 5.0 to 8.0, to generate an acellular graft prior to implantation (see U.S. Pat. No. 5,720,777) has also been described. However, none of these methods have proven successful in completely preventing mineralization. Thus, there remains a need for a postimplantation method useful in removing mineralized deposits on the tissue postimplantation.

Atherosclerotic calcification is an organized, regulated process similar to bone formation that occurs only when other aspects of atherosclerosis are also present. Calcium phosphate, in the crystalline form of carbonated apatite (dahllite), which contains 40% calcium by weight, precipitates in diseased coronary arteries by a mechanism similar to that found in active bone formation and remodeling (Bostom, K., et al., *J. Clin. Invest.* 91:1800–9, 1993; Lowenstam, H. A., and Wiener, S., *On Biomineralization*, Oxford University Press, N.Y). This was previously thought to be calcium phosphate (hydroxyapatite, $Ca_3[-PO_4]_2 Ca[OH]_2$). Atherosclerotic calcification begins as early as the second decade of life, just after fatty streak formation (Stary, H. C., *Eur. Heart J.* 11l(Suppl. E):3–19, 1990). The lesions of younger adults have revealed small aggregates of crystalline calcium phosphate among the lipid particles of lipid cores (Stary, H. C., et al., *Circulation* 92:1355–74, 1995). Calcific deposits are found more frequently and in greater amounts in elderly individuals and more advanced lesions (Doherty, T. M, and Detrano, R. C., *Calcif. Tissue Int.* 54:224–30, 1994). In most advanced lesions, when mineralization dominates the picture, components such as lipid deposits and increased fibrous tissue may also be present. The biochemical sequence of events leading to atherosclerotic calcification is not well understood.

Coronary artery calcification is potentially detectable in vivo by the following methods: plain film roentgenography; coronary arteriography; fluoroscopy, including digital subtraction fluoroscopy; cinefluorography; conventional, helical, and electron beam computed tomography ("EBCT"); intravascular ultrasound ("IVUS"); magnetic resonance imaging; and transthoracic and transesophageal echocardiography. In current practice, fluoroscopy and EBCT are most commonly used to detect coronary calcification noninvasively, while cinefluorography and IVUS are used by coronary interventionalists to evaluate calcification in specific lesions before angioplasty.

Histopathological investigation has shown that plaques with microscopic evidence of mineralization are generally larger and associated with larger arteries than are plaques or arteries without calcification. The relation of arterial calcification to the probability of plaque rupture is unknown. However, correlative studies indicate that patients with greater amounts of coronary calcification are more likely to suffer a clinical event compared with patients without calcification or lesser amounts (Detrano, R. C., et al., *J. Am. Coll. Cardiol.* 24:354–8, 1994). There is evidence linking radiographically detectable coronary calcium to future coronary heart disease events of death and infarction, which suggests that this link is strongest in symptomatic and very high-risk subjects (Naito, S., et al., *J. Cardiol.* 20:249–258, 1990).

SUMMARY OF THE INVENTION

This invention is based on the discovery that acid can be used to demineralize cardiovascular tissue in situ or in vitro, such as a calcified bioprosthetic heart valve or a calcified atherosclerotic lesion.

One aspect of the invention is a method for reducing mineralization of a cardiovascular tissue in a subject, by contacting the cardiovascular tissue with an acidic treatment solution for a period of time sufficient to reduce mineralization.

Another aspect of the invention is a balloon catheter assembly for infusion of a cardiovascular tissue having a mineralized area. This assembly comprises an elongated, flexible catheter having a relatively small diameter for insertion into the vessel and has two toroid-shaped balloons attached in series. These balloons have an inner surface, which is defined as the surface on the first balloon which faces the surface of the second balloon. In addition, an inflation means is communicatively connected with the first and second balloons which can be used to inflate the first and second balloons after insertion of the catheter into a vessel of the cardiovascular tissue, thus defining a segment of the vessel. The assembly also has an infusion means for infusing an acidic treatment material into the defined segment of the vessel, and an extraction means for extracting the acidic treatment material.

Another aspect of the invention is a method for infusing a demineralization solution into a cardiovascular tissue of a subject, comprising inserting a catheter into the cardiovascular tissue so that the catheter defines a blood flow passage, occluding a region within the cardiovascular tissue by inflating two balloons, one of which balloon defines the proximal end of the region and one of which defines the distal end of said region, and infusing an acidic treatment solution for a period of time sufficient to reduce mineralization.

In yet another embodiment a catheter assembly for infusion of a cardiovascular tissue is provided, where the tissue has a mineralized area. The catheter assembly includes a flexible catheter having a relatively small diameter for insertion into the vessel, where the flexible catheter has a flexible cup secured to the distal end of the catheter. A lumen extends through the flexible catheter and communicates with the flexible cup, such that an acidic treatment solution can be infused into an area defined by the cup.

In a further embodiment a catheter assembly for a valve that has a proximal side and a distal side, and a mineralized area, is provided. The assembly includes a flexible catheter with a first and a second lumen, where the distal end of first lumen is secured to a flexible cup which is placed adjacent to the proximal side of the valve when in use. The first lumen is operatively connected with a means for infusing an acidic treatment solution. The second lumen of the catheter extends through the valve. The distal end of the second lumen is secured to an additional flexible cup which is placed adjacent to the distal side of the valve when in use. An outlet exits on the second lumen, and the second lumen is operatively connected with an extraction means for removing the acidic treatment solution.

DESCRIPTION OF THE PREFERRED EMBODIMENTS

Figure 1:
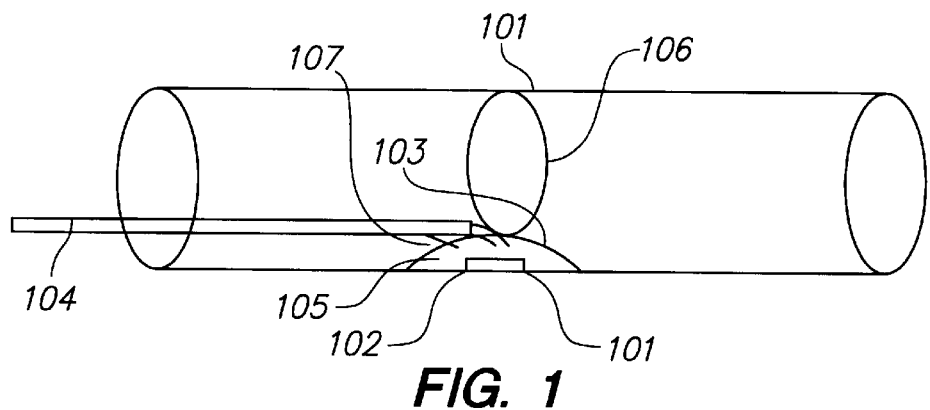
FIG. 1 is a perspective view of a single cup catheter assembly of the invention.

It must be noted that as used herein and in the appended claims, the singular forms "a," "and," and "the" include plural referents unless the context clearly dictates otherwise. Thus, for example, reference to "a rinsing solution" includes a plurality of such solutions and reference to "the vessel" includes reference to one or more vessels and equivalents thereof known to those skilled in the art, and so forth.

Unless defined otherwise, all technical and scientific terms used herein have the same meaning as commonly understood to one of ordinary skill in the art to which this invention belongs. Although any methods, catheters and balloons similar or equivalent to those described herein can be used in the practice or testing of the invention, the preferred methods, devices and materials are now described.

All publications mentioned herein are incorporated herein by reference in full for the purpose of describing and disclosing the catheters, balloons, and methodologies which are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

Definitions

The term "cardiovascular tissue" as used herein refers to the heart, kidney, or any vessel which is part of the cardiovascular system.

The term "prothesis" as used herein refers to any device which is implanted in a subject, preferably a mammal. The term includes heart valves and other heart components, vascular replacements or grafts, artificial hearts, urinary tract and bladder replacements, bowel and tissue resections, left ventricular assist devices, hip replacements, breast implants, artificial tendons, electrodes, and the like. The method of the invention can be used with any prosthesis, however, it is most beneficial for a prosthesis which suffers degeneration or impairment as a result of mineralization. Devices which degenerate or malfunction as a result of mineralization can readily be identified by one of ordinary skill in the art.

The term "valve" as used herein refers to a membranous fold in a canal or passage, which prevents the reflux of the contents of the contents passing through it.

The term "heart valve" or "cardiac valve" as used herein refers to a valve that controls the flow of blood through and from the heart, including the atrioventricular, aortic, and pulmonary trunk valves.

The term "bioprosthetic heart valve" as used herein refers to an artificial cardiac valve composed of biological tissue of any mammal, which can be sterilized and mounted on a plastic or metal supportive structure.

The term "vessel" as used herein refers to any conduit in the circulatory system and includes arteries, arteries, veins, venules, and capillaries.

The term "buffered solution" as used herein refers to an aqueous solution having at least one component which tends to preserve hydrogen ion concentration or pH. The term "buffer" or "buffering agent" refers to a substance capable of maintaining the original acidity or basicity of a solution.

The term "ion exchanger" as used herein refers to a solid or liquid material containing ions that are exchangeable with other ions with a like charge that are present in a solution in which the material is insoluble. The term "chelating agent" as used herein refers to an organic compound in which atoms form more than one coordinate bond with metals in solution. The term "ion exchange" as used herein refers to a chemical reaction in which a mobile hydrated ion of a solid are exchanged, equivalent for equivalent, for ions of like charge in a solution.

The term "fixation" or "fixing" as used herein refers to a process of treating biological material so as to preserve the material from natural decay, including decay by autolysis. Fixation includes methods such as exposing the biological material to glutaraldehyde or formaldehyde.

The term "acid" is as used herein refers to a chemical substance that lowers the pH (increases the hydrogen concentration) when added to an aqueous solution. An acid can be inorganic or organic. The term "organic" acid as used herein refers to any acid the radical of which is a carbon derivative or a compound in which a hydrocarbon radical is united to COOH (a carboxylic acid) or to $SO_3H$ (a sulfonic acid). The term "inorganic" acid as used herein refers to any acid containing no carbon atoms. Acids can be "monobasic" wherein they have but one replaceable hydrogen atom and yield only one series of salts (e.g., HCl) or "polybasic" wherein they contain two or more hydrogen atoms which may be neutralized by alkalies and replaced by organic radicals.

The term "mineralization" as used herein refers to the deposition of a an inorganic composition on a tissue or prosthesis, or the conversion of an organic compound to a simpler inorganic material. The term "calcification" as used herein refers to the deposition of an inorganic composition containing calcium on an organic composition. One example of calcification is the deposition of carbonated apatite on a tissue. Carbonated apatite is deposited as $Ca_{8.3}[PO_4]_{4.3}[CO_3]_x[HPO_4]_y[OH]_{0.3}$, where y decreases increasing age, and x+y is a constant value of 1.7 (see Legaros, R., et al., 1987, Calcified Tiss. Int. 41:137–144, herein incorporated by reference).

The term "apatite" as used herein refers to a group of phosphate minerals that includes ten mineral species and has the general formula $X_5(YO_4)_3Z$, where X is usually $Ca^{2+}$ or $Pb^{3+}$, Y is $P^{5+}$ or $As^{5+}$, and Z is $F^-$, $Cl^-$, or $OH^-$. The term calcium apatite refers to a group of phosphate minerals where X is $Ca^{2+}$. The term "hydroxyapatite" refers to the minerals of the formula $Ca_3[PO_4]_2 \times Ca[OH]_2$.

The term "demineralization" as used herein refers to the removal by any means of an inorganic composition from a tissue or prosthesis. The inorganic composition can be solubilized, or can be removed in solid form, such as in the removal of individual or groups of crystals. The term "decalcification" as used herein refers to the removal of an inorganic composition containing calcium from a tissue or prosthesis. One example of decalcification is the removal of hydroxyapatite ($Ca_3[PO_4]_2 \times Ca[OH]_2$) from a tissue, such as a vessel. The inorganic composition containing calcium can be solubilized, or can be removed in solid form, such as in the removal of individual crystals or groups of crystals.

The term "non-toxic" as used herein refers to a composition which does not cause undue damage to tissue during a treatment period.

The term "ultrasound" as used herein refers to sound waves having frequencies higher than those to which the human ear can respond (i.e., >16 kHz). The upper limit of ultrasonic frequency is one which is not sharply defined but usually taken to be 5 MHz for gases and 500 MHZ for liquids and solids (see Mason, T. J., and Lorimer, J. B., *Sonochemistry: Theory Application and Use of Ultrasound on Chemistry*, Chichester: Ellis Horwood, Oxford, 1988, herein incorporated by reference). The terms "low power ultrasound" and "high frequency ultrasound" as used herein refers to low amplitude (higher frequency) propagation, which is concerned with the effect of the medium on the wave. Low amplitude waves are typically used to measure the velocity and absorption coefficient of the wave in a medium in the 2 to 10 MHZ range. These waves are used, for example, in medical scanning, chemical analysis, and the study of relaxation phenomena. The terms "high power ultrasound" and "low frequency ultrasound" as used herein refers to high energy waves known also as "power ultrasound" between 20 and 100 kHz which are used, for example, for cleaning, plastic welding, and to effect chemical reactivity.

The term "catheter based" as used herein refers to any minimally invasive procedure of use in the cardiovascular system. Specific, non-limiting examples of a catheter based procedure include balloon angioplasty or percutaneous balloon aortic valvuloplasty (BAV).

The term "invasive procedure" or "open procedure" as used herein refers to any procedure with an open surgical field. One specific, non-limiting example of a invasive procedure is bypass surgery. Another specific, non-limiting example of an invasive procedure is intraoperative mechanical debridement (decalcification) of the aortic valve to treat aortic stenosis wherein the aorta is entered surgically (as in a valve replacement procedure) and the calcified deposits are removed using surgical tools, or ultrasound.

Demineralization

The invention provides a method for reducing mineralization of a cardiovascular tissue in a subject, by contacting the cardiovascular tissue with an acidic treatment solution for a period of time sufficient to reduce mineralization. The acidic treatment solution may by any solution with a pH of less than 5.5, preferably the pH is less than 5.5 and more than 1.0, most preferably the pH is less than 4.0 and more than 1.0. The acidic treatment solution can be an inorganic or organic acidic treatment solution. Suitable inorganic acids include, but are not limited to, hydrochloric, nitric, sulfuric, phosphoric, hydroboric, hydrobromic, and hydroiotic acids. For an inorganic acid, the acid can be a concentrated acid, or can be diluted. Upon dilution, the concentration of an inorganic acid will generally be from about 10 N to about 0.01 N, preferably between 5 N to 0.1 N. Organic acids for use with the subject invention include, but are not limited to, any organic acid of one to six ($C_1$ to $C_6$) carbons in length. Organic acids include, but are not limited to formic, acetic, propionic, maleic, butanoic, valeric, hexanoic, phenolic, cyclopentanecarboxylic, benzoic acids, and the like. For an organic acid, the acid can be in concentrated form, or can be diluted. The acidic treatment solution can be composed of either a monobasic or a polybasic acid.

In general an acidic treatment solution can be used at any concentration that does not cause undue tissue damage under the conditions of use. Tissue damage can readily be assessed by one of ordinary skill in the art. For example, tissue treated with the acidic treatment solution can be examined microscopically for evaluation.

The extent to which the delivery system can isolate the mineralized lesion will determine the nature and composition of the acidic treatment solution. In addition, the rate of flow of acidic treatment solution over the mineralized lesion can determine the nature and composition of the acidic treatment solution. A suitable composition can readily be determined by one of ordinary skill in the art based on the nature (size, shape, and location) of the lesion, and the delivery system utilized. The treatment solution can further include calcium-chelating agents, for example, EDTA, crown ethers, and the like.

A buffering agent can be added to the acidic treatment solution in order to maintain the pH of the solution. Suitable buffers include, but are not limited to phosphate buffers, such as sodium phosphate monobasic and dibasic buffers, and phosphate citrate buffer. Other buffering agents, such as Tris(hydroxymethyl)aminomethane (Tris) (Nahas, GG., 1959, Science 129:782), Hepes ($C_8H_{17}N_2O_4SK$) (Good, N. E., et al., 1966, Biochem. 5:467), and the like. Any variety of other buffers well known by those of skill in the art can also be used.

The acidic treatment solution can be introduced at any temperature between the freezing temperature of the acidic treatment solution and about 40° C. As mineral deposits such as carbonated apatite are known to be more soluble in decreased temperatures (see Hydroxyapatite and Related Materials, pp. 93–115, P. W. Brown and B. Constantz, eds., CRC Press, Brown, Boca Ratan, Fla., 1994, herein incorporated by reference), the acidic treatment solution can be introduced at a temperature below about 37° C. Preferably, the acidic treatment solution is introduced at a temperature between the freezing temperature of the acidic treatment solution and 37° C., preferably between about 0° C. and about 20° C., more preferably between about 0° C. and about 10° C. and more preferably between about 0° C. and about 4° C.

The cardiovascular tissue is contacted with the acidic treatment solution for a period of time sufficient to reduce mineralization. The time required for sufficient reduction of mineralization can readily be determined by one of skill in the art. Generally the time period for treatment with the acidic solution depends on the extent of mineralization, and the solution employed, and the type of device utilized, but can range from about two minutes to about two hours or more. In general a time period will be utilized in which undue tissue damage does not occur. In one embodiment, the time period for treatment is from about 5 to about 25 minutes. More than one acidic treatment solution can be contacted with the cardiovascular tissue. In one embodiment, several acidic treatment solutions are contacted with the cardiovascular tissue in series. The extent of demineralization can be monitored after incubation with each acidic treatment solution, or can be monitored during treatment by measuring the amount of mineral removed, or by direct non-invasive observation (e.g., endoscopically or fluoroscopically).

Treatment can be performed under flow conditions, such that the acidic treatment solution is continuously introduced and removed from the mineralized deposit on the cardiovascular tissue at a constant rate. The rate of introduction and removal can be constant, or can be varied. Alternatively, the cardiovascular tissue can be contacted with the acidic treatment solution under static conditions, such that the acidic treatment solution is introduced and left in contact with the cardiovascular tissue for a defined period of time.

Any means of invasive or noninvasive detection and/or quantification known to one of skill in the art can be used to monitor mineralization. Mineralization is potentially detectable in vivo by plain film roentgenography, coronary arteriography, fluoroscopy, including digital substraction fluoroscopy, cinefluorography, conventional, helical and electron beam computed tomography, intravascular ultrasound, magnetic resonance imaging, and transthoracic and transesophageal echocardiography. Any of these means can be used to monitor the reduction in mineralization by the method of the invention. The noninvasive techniques most commonly used in practice, and of use to monitor demineralization of cardiovascular tissue by the method of the subject invention, include conventional and digital fluoroscopy and computed tomography, such as electron beam computed tomography (EBCT) (Reimnuller, R., and Lipton, M. J., *Dynam. Cardiovasc. Imaging* 1:139–145, 1987). A quantitative scoring system has been designed for use with EBCT (Agatston, AS, et al., *J. Am. Coll. Cardiol.* 15:827–832, 1990; Janowitz, W. R., et al., *Am. J. Coll. Cardiol.* 68:1–6, 1991). Cinefluorograph and US are commonly used by to evaluate calcification in specific lesions before invasive procedures, such as during cardiac catheterization (Friedrich, G. J, et al., *Am. Heart J.* 128:435–441, 1994). In addition, transthoracic echocardiography is very sensitive to detection of mitral and aortic valve calcification, although it is not sensitive to detection of mineralization of the coronary arteries (Fernandes, F., et al., *Circulation* 88:2532–2540, 1993).

Following acid treatment, the cardiovascular tissue can be rinsed with a rinsing solution. The rinsing solution can be any solution sufficient to remove or dilute the acidic treatment solution from the cardiovascular tissue, thereby reducing the acidity. The rinsing solution may also be used to remove acid insoluble organic matter that might shield the mineralized deposit from the acidic treatment solution. The rinse solution can also contain chelating agents. In one embodiment, the rinsing solution is a basic solution. The basic solution can be composed of any inorganic or organic base. The basic solution can be concentrated base, or can be a dilute basic solution. The pH of the basic is solution is generally greater than about 9.0. In one embodiment, the basic solution is between a pH of about 10.0 and about 12.0. The basic solution can be a solution of an inorganic base. In one embodiment, the basic solution is a solution of sodium hydroxide (NaOH). In one embodiment, the basic solution is a dilute solution of sodium hypochlorite.

In another embodiment, the rinsing solution is a neutral solution. The neutral rinsing solution can be a buffered solution of physiological pH. Preferably, the neutral rinsing solution has a pH of about 7.0 to about 8.0. More preferably, the neutral rinsing solution has a pH of about 7.4. One nonlimiting example of a neutral rinsing solution is phosphate buffered saline.

The acidic treatment solution can be introduced to the cardiovascular tissue by any means known to one of skill in the art. For example, for treatment of the coronary arteries, a catheter apparatus (see e.g., U.S. Pat. No. 5,167,628, U.S. Pat. No. 4,850,975, herein incorporated by reference) can be utilized, as can any of the assemblies described below. The method of the invention can further be utilized during invasive procedures, such as during cardiopulmonary bypass. The method can be utilized with partitioning devices, for example the device described in U.S. Pat. No. 5,702,368.

In one embodiment, ultrasound can be applied in addition to the acidic treatment solution in order to more effectively demineralize the cardiovascular tissue. Without being bound by theory, it is thought that the ultrasound acts by increasing the rate of dissolution of a mineral deposit in the acidic treatment solution. There are several apparatuses for the application of ultrasound to cardiovascular tissue known to one of skill in the art. For example, U.S. Pat. No. 4,808,153, herein incorporated by reference, describes an ultrasound apparatus to be used in an artery without damaging the artery. The ultrasound can be low frequency ultrasound.

The ultrasound can be applied during the entire time of contact of the cardiovascular tissue with the acidic treatment solution, or ultrasound can be applied for only part of the treatment period. In one embodiment, ultrasound is applied for several short periods of time while the acidic treatment solution is contact with the cardiovascular tissue.

Valves and other tissues can be explanted, demineralized ex vivo, and reimplanted. Alternatively, valves and tissues can be treated in situ, using the devices described below.

Apparatus

Referring now to the drawings, FIG. 1 shows an assembly designed for use in connection with the present invention. A schematic view is shown. The assembly is designed for use in minimally invasive procedures, and in an open surgical field. The assembly is shown in a blood vessel having walls 101 and a mineralized area 102. Catheter 104 has a flexible cup 103 secured near the distal end of the catheter. In one embodiment, the cup can be folded for insertion into the vessel, and then expanded at the desired location in the vicinity of the mineralized area. A defined area 105 is created by the contact of the cup 103 with the vessel wall 101. The catheter is designed to allow infusion of the area 105 with an acidic treatment solution. The catheter is composed of flexible tubing such that it can be situated at any position along a vessel, and should be sufficiently strong so that it withstands the pressure created from the both the flow of the acidic treatment solution and the suction generated during the removal of the acidic treatment solution. Cup 103 can be held in place by maintaining the pressure within area 105 sufficiently below blood pressure, or optionally by a balloon 106 or other means. An ultrasound probe 107 is used to generate ultrasonic energy.

In one embodiment, the catheter 104 is a single lumen catheter. The lumen of the catheter communicates with the interior of the flexible cup 102. An acidic treatment solution can be applied through the catheter to the defined area 105 for the desired time period. Following this time period, the cup is removed, and the acidic treatment solution is allowed to disperse. Alternatively, a device to create suction can be applied to the more proximal end of the catheter so that the acidic treatment solution is drawn away from the defined area via the single lumen. Similarly, following treatment with the acidic treatment solution the rinsing agent can be applied through the single-lumen catheter if desired.

In another embodiment, the catheter 104 is a double-lumen catheter, both of which communicate with the interior of the flexible cup 102. One of the lumens allows the infusion of either an acidic treatment solution or a rinsing solution. The second lumen removes the acidic treatment or rinse solution. Infusion and suction can be alternated, or the two process can be applied simultaneously to create a flow of solution.

In yet another embodiment, catheter 104 is a triple-lumen catheter, all of which communicate with the interior of flexible cup 102. In this embodiment, one of the lumens allows the infusion of an acidic treatment solution, one of the lumens allows the infusion of a rinsing solution, and one of the lumens allow for the application of suction for the removal of solution.

Figure 2:
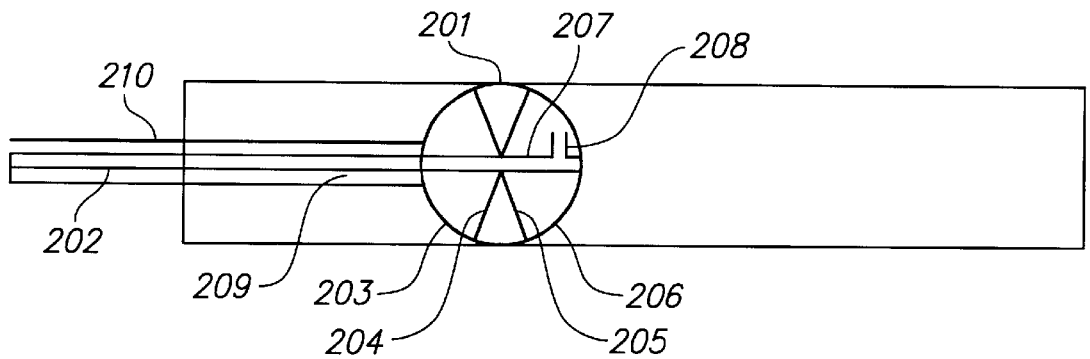
FIG. 2 is a perspective view of a double cup catheter assembly of the invention.

Referring to FIG. 2, a double cup assembly for use with the present invention is shown. The assembly is designed for use in minimally invasive procedures and in an open surgical field. In this apparatus, a first lumen 209 of double lumen inlet catheter 202 is operatively connected to a cup for the application of solution 203. Lumen 209 of the catheter 202 terminates at this first cup 203. This first cup 203 is placed in close proximity to one side 204 of a valve 201 or another projecting structure. One lumen of the catheter 207 passes through the opening of the valve 201, as is terminates at second cup 206. Lumen 207 can be positioned independently of lumen 209 by a guidewire 210. This second cup 206 is placed in close proximity to the on the opposite side 205 of the valve 201 than the first cup 203. In addition, at least one outlet 208 is located on the second lumen of the catheter between the opposing side of the valve 205 and the second cup. An infusion means is attached to the first lumen 209 of the catheter so that acidic treatment solution is delivered to one side 204 of the valve. A removal means is attached to the second lumen 207 of the catheter so that the acidic treatment solution is removed from the opposite side 205 of the valve. Alternatively the infusion means can be attached to the second lumen 207 and the removal means can be attached to the first lumen 209. The solution is preferably applied to the side of the valve opposite the side to be to be treated, and is removed from the mineralized (treated) side. Both lumens of the catheter 202 and 205 are formed of flexible tubing such they can be situated in an appropriate position in close proximity to the valve, and are sufficiently strong to withstand the pressure created from the flow of the acidic treatment solution or the suction generated during the removal of the acidic treatment solution.

Figure 3:
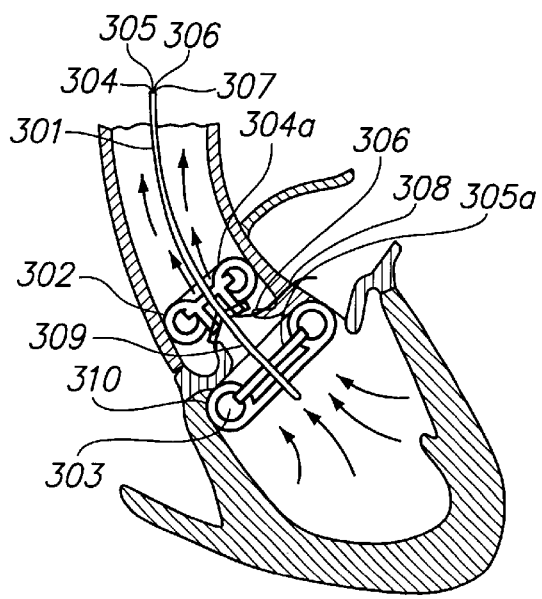
FIG. 3 is a perspective view of a double balloon catheter assembly of the invention.

Referring to FIG. 3, a balloon catheter assembly of the present invention is shown. The assembly is designed for use in minimally invasive procedures or in an open surgical field. The balloon catheter assembly includes a four lumen catheter 301 having two toroid (doughnut)-shaped balloons 302 and 303 attached in series at a distance apart the catheter 301. The catheter 301 terminates just beyond the second balloon 303. The catheter has four lumens 304, 305, 306, and 307. The first lumen 304 communicates with the interior of the first balloon 302 through a lumen branch 304a. Thus, the first balloon can be inflated and deflated by applying positive and negative pressures through lumen 304. The second lumen 305 communicates with the interior of the second balloon 303 though a lumen branch 305a. Thus, the second balloon can be inflated and deflated by applying positive and negative pressure through lumen 305. Lumen 306 is used for the infusion of the acidic treatment solution or the rinsing solution, can open anywhere in the defined area between the two balloons 302 and 303. Lumen 306 can open at one endpoint 308, as shown, or can have multiple branches, each of which open an one endpoint. In the embodiment shown, lumen 306 has one endpoint opening 308 at the inner surface of the first balloon. However, other embodiments can be envisioned, such as one or more opening(s) at sites on region of the catheter between the two balloons 309. Lumen 307 is used for the removal of the acidic treatment solution or the rinsing solution, and can open anywhere in the defined area between the two balloons 302 and 303. Lumen 307 can open at one endpoint 310, as shown, or can have multiple branches, each of which open at one endpoint. In the embodiment shown lumen 307 has one endpoint opening 310 at the inner surface of the second balloon. However, other embodiments can be envisioned, such as one or more opening(s) at sites on the catheter between the two balloons 309.

EXAMPLES

The following examples are intended to illustrate but not to limit the invention in any manner, shape, or form, either explicitly or implicitly. While they are typical of those that might be used, other procedures, methodologies, or techniques known to those skilled in the art may alternatively be used.

Example 1

Human Aortic Valve Tests in vitro

Calcified aortic heart valves are removed operatively during valve replacement surgery and used as an in vitro test system to optimize methods of demineralization. For these studies, a comparison of different acidic treatment solutions is performed. In addition, the acidic treatment solutions are contacted with the calcified aortic valves for varying periods of time. The following solutions and conditions are examined: 0.1 M HCl, 1.0 M HCl, concentrated HCl, 0.1 M HCl+0.01 M EDTA, 1.0 M HCl+0.01 M EDTA, concentrated HCl+0.1 M EDTA, 0.1 M $H_2SO_4$, 1.0 M $H_2SO_4$, 0.1 M $H_2SO_4$+0.01 M EDTA, 1.0 M $H_2SO_4$+0.1 M EDTA, 1.0 M formic acid, concentrated fromic acid, 1.0 M formic acid +0.1 M EDTA, 1.0 M acetic acid, concentrated acetic acid, 1.0 M acetic acid and 0.1 M EDTA, 1.0 M succinic acid, 1.0 M succinic acid +0.1 M EDTA.

Explanted valves are weighed after thorough washing. Each solution (15 ml) is placed in a beaker with a calcified, explanted valve. Replicates are maintained at 4° C., 10° C. and 25° C., and weight loss is measured at 5, 10, 30, 60, 90 and 120 minutes of incubation in the acidic treatment solution. This experiment is repeated, maintaining the valves and solutions in a ultrasonic bath at 25 MHz.

During the course of treatment, calcium and phosphate concentration released from the test valves are measured, and rates of demineralization are determined. The valves are evaluated for the extent of remaining biomineralization and the extent of tissue damage (if any) after each experimental protocol. Physiological function tests are also performed following the contact with the acidic treatment solution.

The following parameters are evaluated and optimized alone in combination: pH, temperature, and sonic power. The carbonated apatite of biomineralized heart valve tissue is more soluble under acidic conditions. The pH ranges to be evaluated are below about 7.0, typically below about 4.0, and optimally about 1.0. The carbonated apatite of biomineralized heart valve tissue is more soluble at colder temperatures. Temperatures to be evaluated are below body temperature (37° C., typically below 5° C., and optimally near 0° C. Sonic power accelerates reactions in solution. Sound frequencies in the range of 20 kHz to 100 kHz are evaluated, typically about 25 kHz.

Example 2

Human Aortic Valve Tests in a Porcine Model

The most common causes of pure aortic stenosis are calcification of bicuspid valves, commissural fusion, degenerative calcification of tricuspid valves, cuspid fibrosis, and postinflammatory calcification of rheumatic origin. Calcified valves removed from human patients are transplanted into pigs. The animals are allowed to recover, and are then subjected to demineralization therapy with the acidic treatment solution. Devices for applying the acidic treatment solution to the stenotic aortic valves are made to either apply to a beating heart or a stopped heart. Devices applied to the beating heart will introduce the acidic treatment solution at a specific temperature and pH in conjunction with sonic power. For example, the acidic treatment solution is introduced across the base of the valve leaflets through a half doughnut shaped device as depicted in FIG. 3, semicircular in cross section on either side of the valve. Devices applied to the stopped heart, or to a bypassed heart which is still beating, will isolate the aortic valve region form the blood stream and circulate and cycle demineralizing solution through the aortic valve region.

The surgeon attempts to create grain boundary separations between individual grains of the carbonated apatite (dahllite), which composes the calcified tissue. Acidic solutions preferentially dissolve the calcium phosphate mineral at grain boundaries. Combined with ultrasonic power, this serves to loosen individual grains without having to dissolve the entire grain. Loose grains are removed with the circulating solution. Organic matrices entombed within the mineralized deposit may shield the mineral phase from the acidic treatment solution, necessitating solutions that are efficient in removing elements of an organic matrix from the grain boundary regions. Thus, one can supplement the acidic treatment solution with proteases, surfactants, detergents, oxidants and the like, at concentration sufficient to remove organic matrix without undue damage to the tissue under treatment. Alternatively, the supplements can be provided in one or more individual solutions and alternated with the acidic treatment solution. The removal of the organic matrix exposes the mineral to subsequent treatment with acidic treatment solution. Various solutions can be suction-pumped through the treated region through tubing. In this embodiment, both in-current and out-current flows are present. The out-current flow carries the cycled solutions, the dissolved ions from the mineral with organic debris, and loose pieces of mineralized deposits which become dislodged from the attached mineralized mass before dissolution of the mineral deposit is complete. Different solutions are cycled through the test region from a single site outside the body. Progression of demineralization is monitored using standard echocardiographic methods.

Example 3

Formulation

A.) A suitable formulation for acidic treatment under a constant flow rate comprises:

| | |
|---|---|
| Formic acid (concentrated) | 10% |
| Sodium dodecyl sulfate (SDS) | 0.1% |
| $H_2O$ qs | 100% |

B.) An alternative formulation for acidic treatment under a constant flow rate comprises:

| | |
|---|---|
| HCl (concentrated) | 10% |
| EDTA | 0.1% |
| $H_2O$ qs | 100% |

C.) An alternative formulation for acidic treatment under a constant flow rate comprises:

| | |
|---|---|
| Phosphoric acid (concentrated) | 10% |
| $H_2O$ qs | 100% |

D.) An alternative formulation for acidic treatment under a constant flow rate comprises:

| | |
|---|---|
| Sulfuric acid (concentrated) | 10% |
| $H_2O$ qs | 100% |

E.) An alternative formulation for acidic treatment under a s lower rate or under static conditions comprises:

| | |
|---|---|
| Tris HCl | 0.1 M | pH adjusted to 4.2 with concentrated HCl.

Example 4

The Sheep Model

To evaluate the efficacy of an acidic treatment solution in vivo, a sheep model is utilized. In this model, porcine aortic valved conduits are treated with 0.625% glutaraldehyde in vitro, and transplanted into the descending thoracic aorta in juvenile sheep (see Chanda, J., et al., 1997, Biomaterials 18:1317–1321, herein incorporated by reference). The calcification of the transplanted porcine valves are then analyzed by gross inspection, radiography, light, transmission, and surface scanning electron microscopy, or calcium analysis by absorption spectroscopy can be performed (see Schoen, F. J., et al., 1994, J. Thorac. Cardiovasc. Surg. 108:880–887). Any tissue damaged is also assessed by light microscopy.

Example 5

Analysis of Aortic Valve Mineralization

Two human aortic heart valves were removed during routine valve replacement therapy. These valves were dissected to separate mineralized deposits on the valve leaflets. The deposits where strongly adherent to the valve tissue and were incorporated into the structure of the leaflets as nodules. Both valves had extensive mineralize nodule formation. The nodules were hard and could not be fractured by hand. Contact x-rays were taken t document the extent and distribution of the mineralized nodules in the valve tissue. The mineralized areas demonstrated a radioscopy similar to well mineralized bone.

Figure 4A:
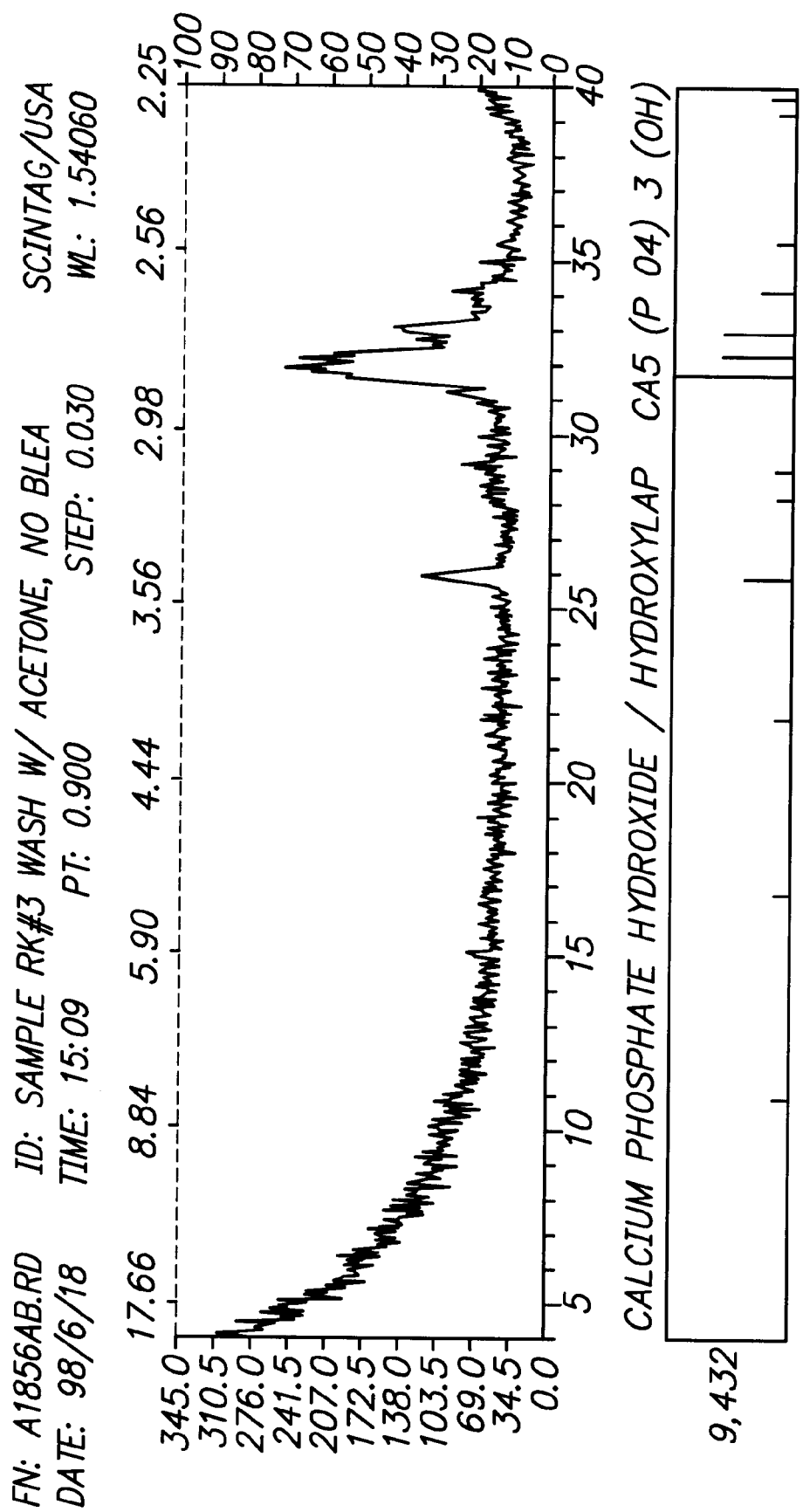
FIG. 4A is an x-ray defraction pattern (XRD) of an intact mineralized lesion directly isolated from an excised human aortic heart valve leaflet.
Figure 4B:
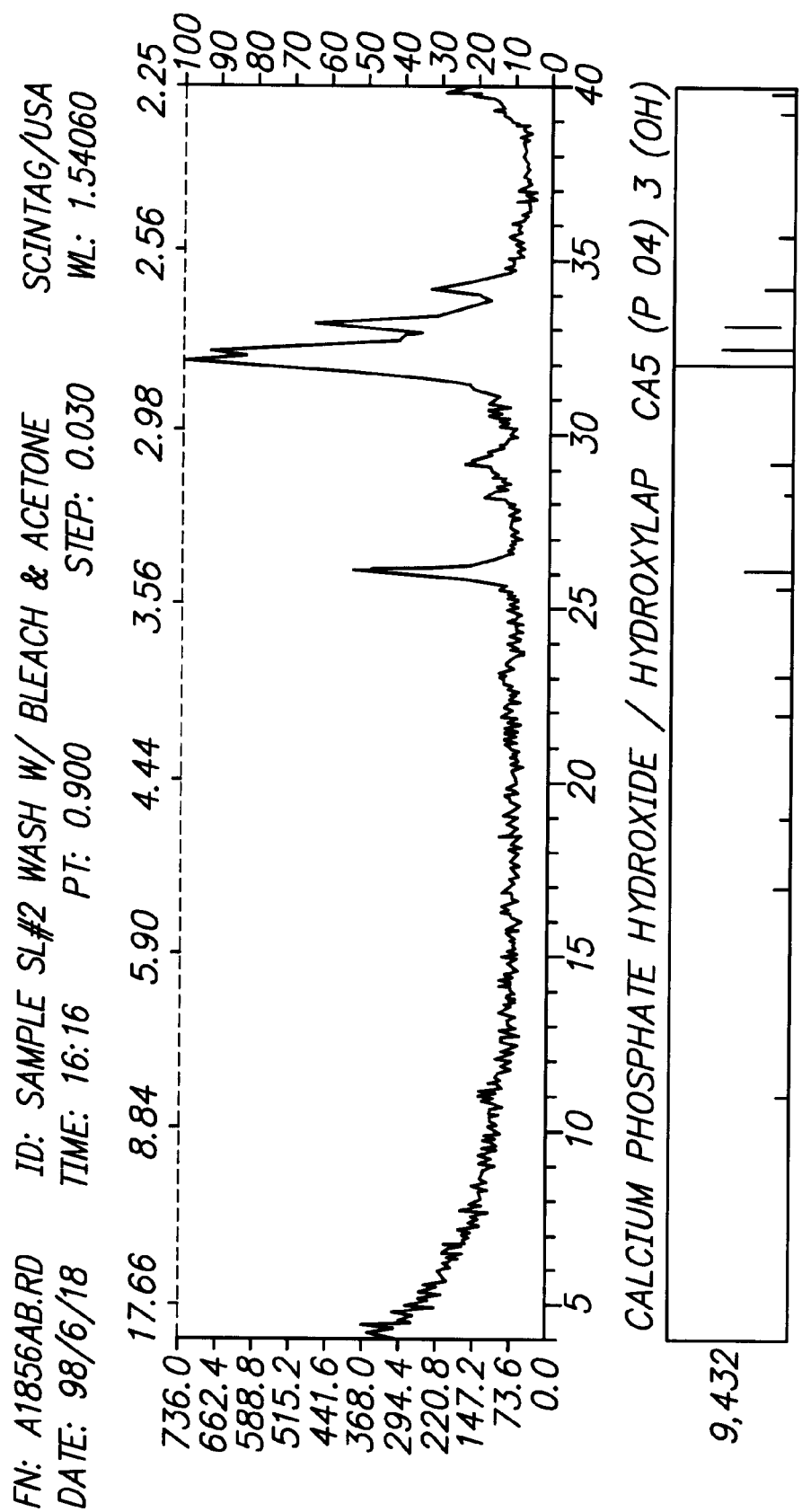
FIG. 4B is a x-ray difraction pattern of a mineralized lesion with the organics removed by treatment with sodium hypochlorite.
Figure 5A:
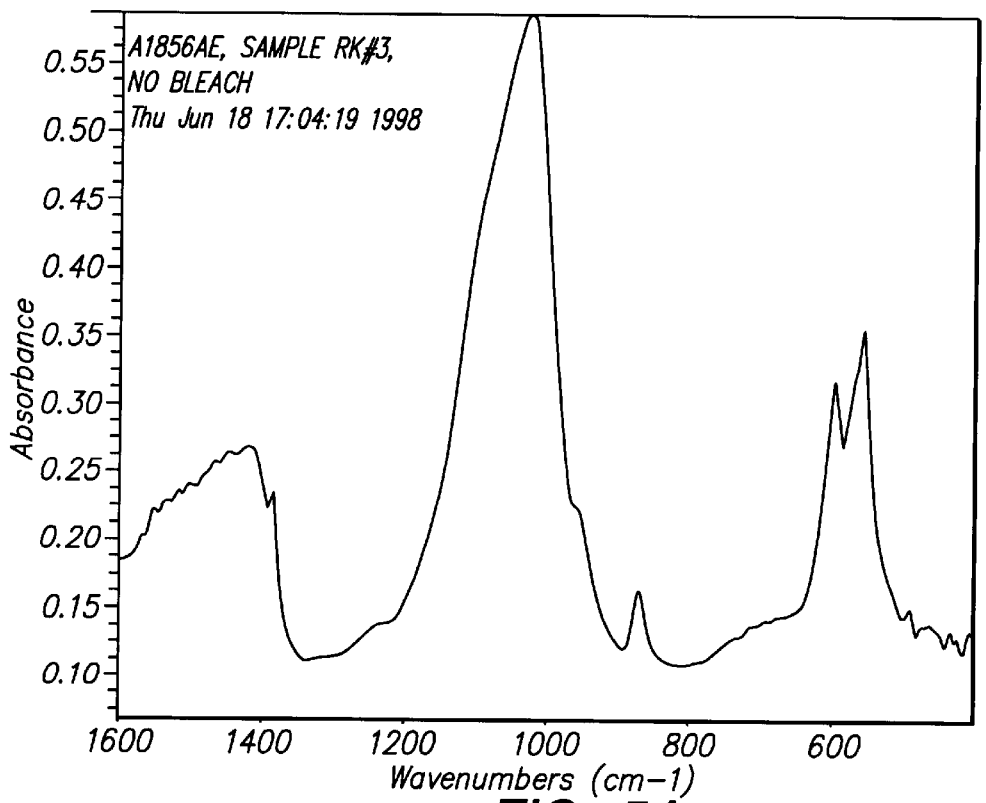
FIG. 5A is a Fourier transform infra-red (FTIR) spectrogram of an intact mineralized lesion directly isolated from an excised human aortic heart valve leaflet.
Figure 5B:
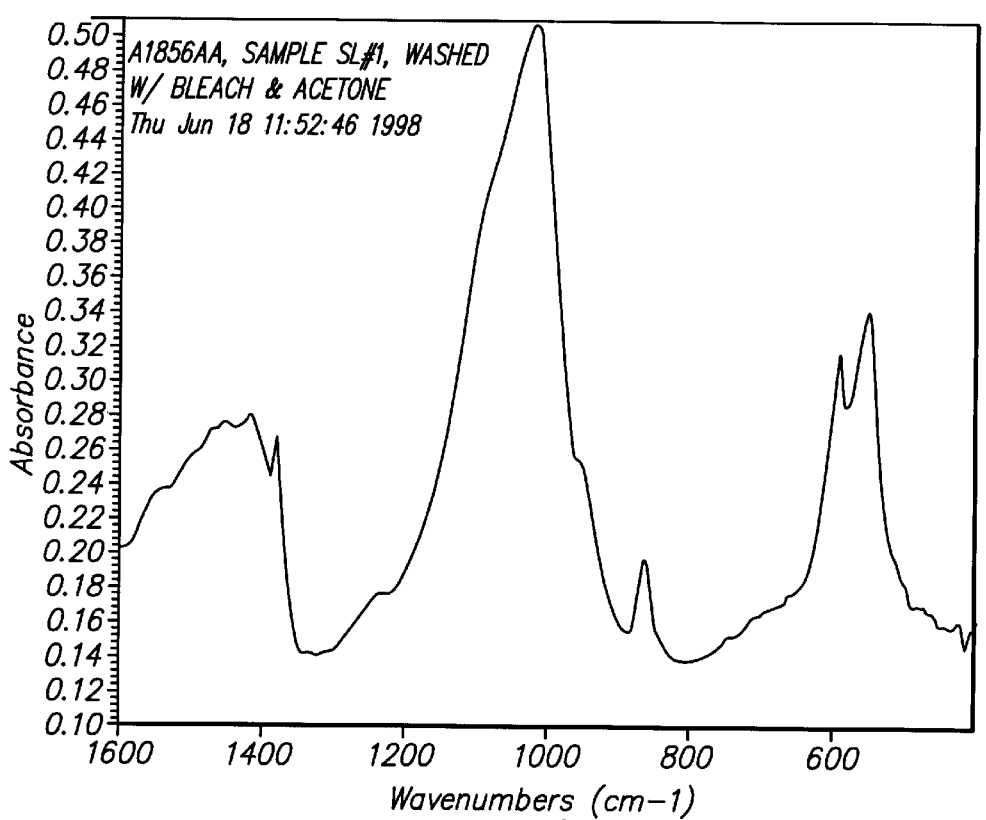
FIG. 5B is a FTIR of a mineralized lesion with the organics removed by treatment with sodium hypochlorite.

X-ray diffraction (XRD, see FIGS. 4A and 4B) and Fourier Transform Infra Red Spectroscopy (FTIR, see FIGS. 5A and 5B) were performed using standard procedures (see Constantz, B. R., et al., 1995, Science 267: 1796–1799, herein incorporated by reference) on the removed samples both directly (see FIGS. 4A and 5A) and following removal of most organic material with sodium hypochlorite (CLOROX bleach, see FIGS. 4B and 5B). The XRD pattern of the mineralized tissue, both with and without the organics removed, showed the characteristic peaks of apatite. The reflections were poorly crystalline in nature, indicating small crystal size and low levels of crystalline order. The FTIR spectrogram of the mineralized tissue, both with and without the organics removed, further identify the mineralized deposit as apatite that contains substantial carbonate, termed a carbonated apatite (mineral name, dahllite).

Samples were prepared for scanning electron microscopy, using the methods of Constantz, B. R., et al., 1986 (In: *Reef Diagenesis*, Schroeder, J., and Puser, B., (eds.), Springer-Verlag). The size of the crystals composing the mineralized deposit were less than one micron across. The solubility of the crystals in this size range is expected to modify by an order of magnitude due to their increased surface are to volume ratio (see Constantz, B. R., et al., 1986, supra).

The composition of the "calcific deposits" are not hydroxyapatite as commonly published, rather they are a carbonated apatite, dahllite, which is expected to be considerably more soluble than hydroxyapatite. Also the size and crystallinity of the crystals of dahllite comprising these deposits are that of very small, high surface are to volume ratio crystallites whose diffraction patterns indicate a very low degree of crystalline order, further increasing their solubility.

Although the invention has been described with reference to the presently preferred embodiment, it should be understood that various modifications can be made without departing from the spirit of the invention. Accordingly, the invention is limited only by the following claims.

What is claimed is:

1. A method for reducing mineralization of a cardiovascular tissue, comprising contacting the cardiovascular tissue with an acidic treatment solution having a pH of less than about 4 for a period of time sufficient to reduce mineralization.

2. The method of claim 1, further comprising applying ultrasonic vibration to the cardiovascular tissue.

3. The method of claim 1, further comprising rinsing said cardiovascular tissue with a rinsing solution.

4. The method of claim 1, wherein said acidic treatment solution comprises an inorganic acid.

5. The method of claim 1, wherein said acid comprises a Tris acid.

6. The method of claim 1, wherein said acidic treatment solution has a pH of about 5.5 to about 1.0.

7. The method of claim 1, wherein said contacting is performed at a temperature from about the freezing temperature of the acidic treatment solution to about 37° C.

8. The method of claim 7, wherein said contacting is performed at a temperature from about 0° C. to about 10° C.

9. The method of claim 1, wherein said cardiovascular tissue is a vessel.

10. The method of claim 9, wherein said vessel is a graft.

11. The method of claim 1, wherein said cardiovascular tissue is a heart valve.

12. The method of claim 11, wherein said heart valve is a prosthetic heart valve.

13. The method of claim 12, wherein said prosthetic heart valve is a bioprosthetic heart valve.

14. The method of claim 1, wherein said contacting is in vivo.

15. A method for infusing a demineralization solution into a cardiovascular tissue of a subject, comprising:

inserting a catheter into the cardiovascular tissue so that the catheter defines a blood flow passage, occluding a region within said cardiovascular tissue by inflating a first and a second balloon, wherein said first balloon defines the proximal end of said region and said second balloon defines the distal end of said region, infusing an acidic treatment solution having a pH of less than about 4 for a period of time sufficient to reduce mineralization.

16. The method of claim 15, wherein said acid is an inorganic acid .

17. The method of claim 15, wherein said acidic treatment solution has a pH of about 5.5 to about 1.0.

18. The method of claim 15, wherein said cardiovascular tissue is a vessel.

19. The method of claim 18, wherein said vessel is a graft.

20. The method of claim 15, wherein said cardiovascular tissue is a heart valve.

21. The method of claim 20, wherein said heart valve is a prosthetic heart valve.

22. The method of claim 21, wherein said prosthetic heart valve is a bioprosthetic heart valve.

\* \* \* \* \*